United States Patent [19]

Dutra

[11] 4,089,671
[45] May 16, 1978

[54] N,N'-METHYLENEBIS-[O,O-DIARYL N-PHOSPHONOMETHYLGLYCINONITRILES]

[75] Inventor: Gerard A. Dutra, Ladue, Mo.

[73] Assignee: Monsanto Company, St. Louis, Mo.

[21] Appl. No.: 807,954

[22] Filed: Jun. 20, 1977

Related U.S. Application Data

[63] Continuation-in-part of Ser. No. 750,327, Dec. 13, 1976.

[51] Int. Cl.² ............................ A01N 9/36; C07C 9/40
[52] U.S. Cl. ............................................. 71/86; 71/87; 260/932
[58] Field of Search ....................... 260/932; 71/86, 87

[56] References Cited

U.S. PATENT DOCUMENTS

| | | | |
|---|---|---|---|
| 2,635,112 | 4/1953 | Fields | 260/932 X |
| 3,560,479 | 2/1971 | Pande | 260/932 X |
| 3,907,937 | 9/1975 | Dixon et al. | 71/87 X |
| 4,008,296 | 2/1977 | Barton | 260/940 |

*Primary Examiner*—Joseph Paul Brust
*Attorney, Agent, or Firm*—Arnold H. Cole; Donald W. Peterson

[57] ABSTRACT

N,N'-methylenebis-[(O,O-diaryl N-phosphonomethylglycinonitriles] are described as well as a process for producing same. These compounds are useful as herbicides.

28 Claims, No Drawings

N,N'-METHYLENEBIS-[O,O-DIARYL N-PHOSPHONOMETHYLGLYCINONITRILES]

This application is a continuation-in-part of application Ser. No. 750,327, filed Dec. 13, 1976.

This invention relates to novel N,N'-methylenebis-[O,O-diaryl N-phosphonomethylglycinonitriles] which are useful as herbicides. This invention further relates to herbicidal compositions and to herbicidal methods employing said bis-glycinonitriles.

Copending application Ser. No. 750,327, filed Dec. 13, 1976, discloses and claims certain mono and diaryl esters of N-phosphonomethylglycinonitrile, and the strong acid addition salts thereof. The instant application discloses certain N,N'-methylenebis derivatives of such compounds. These derivatives are themselves novel organic chemical compounds, and they have been found to have particular utility as post-emergent herbicidal agents.

The N,N'-methylenebis-[O,O-diaryl N-phosphonomethylglycinonitriles] of the invention can be illustrated by the formula

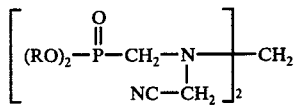

wherein R represents phenyl or naphthyl, and R can contain up to two constituents selected from halogen, lower alkyl, lower alkoxy and lower alkylthio. As employed herein, the term "lower" designates those straight or branched chain alkyl radicals having up to four carbon atoms. The preferred alkyl radicals are those having no more than two carbon atoms, and the preferred halogen is chlorine.

It has been found that the N,N'-methylenebis compounds of the present invention can be prepared either concurrently with or sequentially from the O,O-diaryl N-phosphonomethylglycinonitriles of the above-mentioned copending application. The concurrent preparation is carried out by forming an admixture consisting essentially of a phosphorous acid ester of the formula

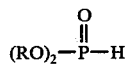

wherein R is as above defined and 1,3,5-tricyanomethyl-hexahydro-1,3,5-triazine (also named N-methyleneglycinonitrile trimer) of the formula

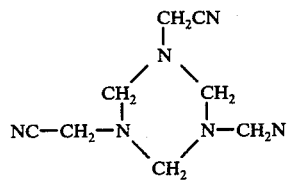

Said admixture is heated to a temperature sufficiently elevated to initiate and sustain the reaction of the phosphorous acid ester with the triazine to produce the desired products.

Although a solvent is not necessary in the process of the instant invention, it is sometimes desirable to employ a solvent for convenience and ease of reaction. A solvent is also useful to control the temperature of the reaction. The solvent employed is one in which the triazine is soluble and which does not react with either of the reactants. Such inert solvents include acetonitrile, ethyl acetate, tetrahydrofuran and the like.

It has been found that the reaction temperature can be as low as about 25° to about 110° C. Higher temperature can be employed but no commensurate advantages are obtained thereby since the reaction is essentially complete by the time the temperature reaches about 85° C.

As can be seen from the above formulas of the reactants, the ratio of the phosphorous acid ester to triazine should be 3 to 1 for best results. Higher or lower ratios could be employed but no commensurate advantages are obtained thereby, since at higher ratios excess phosphorous acid ester would have to be separated and at lower ratios of ester to triazine by-product formation is possible.

The reaction is generally conducted at atmospheric pressure for economy. However, higher or lower pressures can be employed although no commensurate advantages are recognized thereby.

The reaction is permitted to proceed until all of the phosphorous acid ester and triazine are consumed as determined by nuclear magnetic resonance analysis. If such analysis shows the presence of impurities in the form of unreacted excess starting materials or solvent, the reaction mixture can be subjected to vacuum concentration. Then, the desired product is isolated and purified by crystallization or chromatographic procedures. Care should be taken during these latter procedures to avoid hydrolysis of the ester portion of the molecule.

Using a sequential approach, the O,O-diaryl N-phosphonomethylglycinonitrile is first prepared according to the methods described in said copending application. This product is then admixed with a hindered phenylazomethine and heated under vacuum. An intermediate azo-adduct is believed to be formed, after which heating is continued until evolution of the hindered aniline is complete. The reaction mixture is then worked up to isolate the desired methylenebis product.

The hindered phenylazomethines which are useful in the practice of this invention are those wherein the phenyl ring contains substituents at both ortho positions. These substituents can both be lower alkyl, except for the case of 2,6-di-t-butyl. In addition, a halogen or a lower alkoxy substituent can be employed in one ortho position with the other being said lower alkyl. Other positions of the ring may also be substituted. Examples of the hindered phenyl groups include 2-methyl-6-ethyl, 2,6-diethyl, 2-methyl-6-t-butyl, 2-chloro-6-t-butyl, 2-bromo-6-t-butyl, 2-methoxy-6-t-butyl, and the like. It has generally been found that without the above-defined hindrance, the azomethine reactant will trimerize to a hexahydrotriazine.

The glycinonitrile reactants prepared according to the methods described in said copending application will often contain phenolic impurities which can interfere with the production of the desired methylenebis compounds of this invention. It is therefore preferred to first prepare a strong acid salt of the glycinonitrile which precipitates to permit ready separation of said impurities. This salt is thereafter neutralized to obtain the desired glycinonitrile reactant. Care should be taken during the neutralization to avoid hydrolysis of the aryl ester groups.

The reaction of the glycinonitrile and the azomethine begins at room temperature based upon analysis by nuclear magnetic resonance. Temperatures up to about 125° C. can be employed, although a range of about 60°–80° C. is preferred. While the reaction proceeds well at atmospheric pressure, the hindered aniline which forms may then react with the desired product to give an undesired adduct. It is therefore preferred to remove said hindered aniline as it is produced, and this is most efficiently accomplished by using reduced pressure conditions whereby the aniline distills over during the reaction.

The molar ratio of glycinonitrile to azomethine is preferably about 2:1. Higher or lower ratios can be employed, but these may reduce product yields by causing mixtures with unreacted starting materials and said intermediate azo-adduct. A basic catalyst can be used if desired, although the reaction proceeds to the desired product in its absence.

The following experiments serve to further illustrate the invention, all parts being parts by weight unless otherwise specifically set forth.

EXAMPLE 1

An acetonitrile solution (10 ml.) of di(3,4-dimethylphenyl)phosphite (8.7 g., 0.03 mole) was added to an acetonitrile solution (50 ml.) of 1,3,5-tricyanomethyl-hexahydro-1,3,5-triazine (2.04 g., 0.01 mole) and the mixture was heated at 55° C. for 90 hr. Filtration of the solid present and evaporation of the solvent gave a burgundy colored oil which by n.m.r. analysis contained the desired product and the aminal of this product. Chromatography of the oil (8.0 g.) over silica gel (450 g.) with 50% cyclohexane/50% ethyl acetate (60 ml. fractions) gave O,O-di(3,4-dimethylphenyl) N-phosphonomethylglycinonitrile in fractions 30–41. Fractions 20–25 from the chromatographic column, upon evaporation of the solvent, gave 1.62 g. of an oil, $n_D^{22}$ = 1.5387. Crystallization of this oil from carbon tetrachlorideisooctane afforded a white solid identified as N,N'-methylenebis-[O,O-di(3,4-dimethylphenyl) N-phosphonomethylglycinonitrile], m.p. 79°–80° C.

EXAMPLE 2

An acetonitrile solution (100 ml.) of di(m-tolyl)phosphite (10.7 g., 0.04 mole) and 1,3,5-tricyanomethyl-hexahydro-1,3,5-triazine (2.72 g., 0.0133 mole) was heated at 50° C. for 3 days. The solution turned a wine red color, and the solvent was evaporated leaving 12.4 g. of a red oil (92.4% recovery). The oil (9.0 g.) was chromatographed over silica gel eluted with 60% cyclohexane/40% ethyl acetate with 60 ml. fractions taken. Fr. 45–63 were pure O,O-di(m-tolyl) N-phosphonomethylglycinonitrile. Fractions 28–40 from the chromatograph were evaporated in vacuo to yield a solid having a melting point of 113°–114° C. and identified as N,N'-methylenebis-[O,O-di(m-tolyl) N-phosphonomethylglycinonitrile] which gave the following analysis.

Calc'd: C, 62.50; H, 5.69; N, 8.32. Found: C, 62.58; H, 5.72; N, 8.23.

EXAMPLE 3

Di(p-methylthiophenyl)phosphite (30.4 g., 0.082 mole) and 1,3,5-tricyanomethyl-hexahydro-1,3,5-triazine (5.6 g., 0.0275 mole) were heated to 80° C. for 1 hour. The resulting dark red-brown oil was allowed to cool to room temperature and dissolved in carbon tetrachloride (200 ml.). This solution was added to silica gel (30 g.), stirred and filtered, and then again added to silica gel (20 g.) with stirring and filtering. Half of the resulting solution was adhered onto silica gel (12.5 g.) and chromatographed over silica gel (450 g.) eluted with 60% cyclohexane/40% ethyl acetate (60 ml. fractions). Fractions 28–39 were combined to give 1.2 g. of N,N'-methylenebis-[O,O-di(p-methylthiophenyl) N-phosphonomethylglycinonitrile], $n_D^{22}$ = 1.6151.

EXAMPLE 4

Diphenyl phosphite (234 g., 1.0 mole) was added to an acetonitrile solution (300 ml.) of 1,3,5-tricyanomethyl-hexahydro-1,3,5-triazine (68 g.; 0.333 mole) and heated at 75°–82° C. for 3 hours. The solution was cooled and concentrated in vacuo to give a black oil which was mainly the glycinonitrile.

A sample of this oil (101 g.) was adhered onto silica gel (which was dissolved in chloroform, more silica gel added and solvent evaporated), and this material was chromatographed over silica gel (1.1 kg.) eluted with chloroform (1 liter fractions). Fractions 13–14 were combined, concentrated and recrystallized from dichloromethane-cyclohexane to give 51 g. of O,O-diphenyl N-phosphonomethylglycinonitrile.

Fractions 11–12 were combined, concentrated to an oil, and solids were removed by filtration. The mother liquor from Fractions 11–12 was chromatographed over silica gel (760 g.) eluted with 60% cyclohexane/40% ethyl acetate (100 ml. fractions). Fractions 40–49 were combined and recrystallized from cold carbon tetrachloride to give N,N'-methylenebis-[O,O-diphenyl N-phosphonomethylglycinonitrile], m.p. 98°–99° C. The product gave the following analysis.

Calc'd: C, 60.39; H, 4.90; N, 9.09. Found: C, 60.59; H, 4.79; N, 8.97.

EXAMPLE 5

A mixture of O,O-diphenyl N-phosphonomethylglycinonitrile (78.05 g.; 0.258 mole) and 2,6-diethylphenylazomethine (21.06 g.; 0.129 mole) was placed in a kugelrohr distillation apparatus with a catalytic amount (about 10 mg.) of sodium methoxide. The mixture was heated at 65°–75° C. under vacuum (0.02–0.07 mm.) for about 1 hour. Distillation of 2,6-diethylaniline began almost at once, and it continued for almost 1 hour. The vacuum was released, and carbon tetrachloride (500 ml.) was added until the oil recrystallized. The hot solution was filtered and allowed to cool to room temperature. Solids were collected and washed with cold carbon tetrachloride, and the mother liquor was concentrated to yield further solids which were combined for a total of 72.5 g. The product was identified as N,N'-methylenebis-[O,O-diphenyl N-phosphonomethylglycinonitrile], m.p. 100°–100.5° C.

EXAMPLE 6

A mixture of O,O-di(p-methoxyphenyl) N-phosphonomethylglycinonitrile (7.4 g.; 0.02 mole) and 2,6-diethylphenylazomethine (1.63 g.; 0.01 mole) was prepared, and a small exothermic reaction occurred. After about ½ hour the mixture was placed in a kugelrohr distillation apparatus and heated at 60°–70° C. under vacuum (0.1 mm.) for about ½ hour while 2,6-diethylaniline distilled over. The remaining product was cooled, stirred and dissolved in hot carbon tetrachloride. The solution was filtered, after which ether was added to the residual oil and decanted twice. Chloroform is added to the oil, and concentrated then gives a product identified as N,N'-methylenebis-[O,O-di(p-methoxyphenyl) N-phosphonomethylglycinonitrile] as red-tan prisms, m.p. 90°–92° C. This product gave the following analysis.

Calc'd: C, 57.07; H, 5.20; N, 7.61. Found: C, 57.06; H, 5.22; N, 7.63.

EXAMPLE 7

A mixture of O,O-di(4-chloro-3-methylphenyl) N-phosphonomethylglycinonitrile (2.8 g.; 0.007 mole) and 2,6-diethylphenylazomethine (0.57 g.; 0.0035 mole) was prepared, and a slight exothermic reaction occurred. The mixture was placed in a kugelrohr distillation apparatus and heated at 75°–80° C. under vacuum (0.1 mm.) for about ½ hour while 2,6-diethylaniline distilled over. The remaining oil was cooled and then recrystallized from carbon tetrachloride/methyl cyclohexane ether to yield a white solid. The product is identified as N,N'-methylenebis-[O,O-di(4-chloro-3-methylphenyl) N-phosphonomethylglycinonitrile], m.p. 89.5°–90.5° C. This product gave the following analysis.

Calc'd: C, 51.87; H, 4.23; N, 6.91. Found: C, 51.77; H, 4.25; N, 7.01.

EXAMPLE 8

The post-emergence herbicidal activity of various compounds of this invention is demonstrated as follows. The active ingredients are applied in spray form to 14–21 day-old specimens of various plant species. The spray, a water or organic solvent-water solution containing active ingredient and a surfactant (35 parts butylamine salt of dodecylbenzenesulphonic acid and 65 parts tall oil condensed with ethylene oxide in the ratio of 11 moles ethylene oxide to 1 mole tall oil), is applied to the plants in different sets of pans at several rates (kg. per hectare) of active ingredient. The treated plants are placed in a greenhouse and the effects are observed and recorded after approximately 2 weeks or approximately 4 weeks. The data is given in Tables I and II.

The post-emergence herbicidal activity index used in Tables I and II is as follows:

| Plant Response | Index |
| --- | --- |
| 0–24% Injury | 0 |
| 25–49% Injury | 1 |
| 50–74% Injury | 2 |
| 75–99% Injury | 3 |
| All Killed | 4 |
| Species not present at time of treatment | * |

In said Tables, WAT indicates weeks after treatment, and the plant species treated are each represented by a code letter as follows:

| | | | |
| --- | --- | --- | --- |
| A | — Canada Thistle | K | — Barnyard Grass |
| B | — Cocklebur | L | — Soybean |
| C | — Velvet Leaf | M | — Sugar Beet |
| D | — Morning Glory | N | — Wheat |
| E | — Lambsquarters | O | — Rice |
| F | — Smartweed | P | — Sorghum |
| G | — Nutsedge | Q | — Wild Buckwheat |
| H | — Quackgrass | R | — Hemp Sesbania |
| I | — Johnson Grass | S | — Panicum Spp |
| J | — Downy Brome | T | — Crabgrass |

TABLE I

| Compound | WAT | kg/h | A | B | C | D | E | F | G | H | I | J | K |
| --- | --- | --- | --- | --- | --- | --- | --- | --- | --- | --- | --- | --- | --- |
| 1 | 2 | 11.2 | 1 | 1 | 1 | 1 | 2 | 1 | 1 | 1 | 1 | 1 | 2 |
|  | 4 | 11.2 | 1 | 2 | 1 | 2 | 4 | 2 | 2 | 2 | 2 | 2 | 3 |
|  | 2 | 5.6 | 1 | 1 | 1 | 1 | 2 | 1 | 0 | 0 | 1 | 1 | 2 |
|  | 4 | 5.6 | 1 | 2 | 1 | 1 | 4 | 2 | 2 | 1 | 1 | 1 | 2 |
| 2 | 2 | 11.2 | 1 | 1 | 0 | 1 | 1 | 1 | 0 | 0 | 1 | 0 | 0 |
|  | 4 | 11.2 | 1 | 1 | 0 | 1 | 4 | 2 | 1 | 1 | 1 | 0 | 1 |
|  | 2 | 5.6 | 0 | 1 | 0 | 0 | 1 | 0 | 0 | 0 | 0 | 0 | 0 |
|  | 4 | 5.6 | 0 | 1 | 0 | 0 | 1 | 1 | 0 | 0 | 0 | 0 | 1 |
| 3 | 2 | 11.2 | 2 | 2 | 1 | 1 | 4 | 3 | 2 | 1 | 1 | 1 | 3 |
|  | 4 | 11.2 | 2 | 3 | 1 | 1 | 4 | 4 | 2 | 2 | 1 | 1 | 3 |
|  | 2 | 5.6 | 1 | 2 | 1 | 1 | 4 | 3 | 1 | 1 | 1 | 1 | 2 |
|  | 4 | 5.6 | 1 | 2 | 1 | 1 | 4 | 3 | 2 | 2 | 2 | 1 | 3 |
| 4 | 2 | 11.2 | 2 | 3 | 1 | 4 | 4 | 4 | 3 | 3 | 4 | 3 | 3 |
|  | 4 | 11.2 | 3 | 4 | 1 | 4 | 4 | 4 | 4 | 4 | 4 | 3 | 4 |
|  | 2 | 5.6 | 1 | 2 | 1 | 1 | 3 | 4 | 2 | 2 | 4 | 0 | 2 |
|  | 4 | 5.6 | 3 | 3 | 0 | 3 | 4 | 4 | 3 | 3 | 4 | 1 | 3 |
| 6 | 2 | 11.2 | 1 | 1 | 1 | 1 | 3 | 1 | 0 | 0 | 0 | 0 | 2 |
|  | 2 | 5.6 | 1 | 1 | 1 | 1 | * | 1 | 0 | 0 | 0 | 0 | 1 |
| 7 | 2 | 11.2 | 2 | 1 | 1 | 1 | 4 | 1 | 0 | 0 | 1 | 0 | 1 |
|  | 2 | 5.6 | 1 | 1 | 1 | 1 | 3 | 1 | 1 | 1 | 2 | 0 | 3 |

TABLE II

| Compound | WAT | kg/h | L | M | N | O | P | B | Q | D | R | E | F | C | J | S | K | T |
| --- | --- | --- | --- | --- | --- | --- | --- | --- | --- | --- | --- | --- | --- | --- | --- | --- | --- |
| 1 | 2 | 5.6 | 1 | 1 | 2 | 1 | 2 | 1 | 1 | 1 | 1 | 1 | 1 | 0 | 2 | 1 | 1 | 1 |
|  | 4 | 5.6 | 2 | 1 | 2 | 1 | 3 | 2 | 1 | 1 | 3 | 2 | 2 | 1 | 2 | 1 | 1 | 3 |
|  | 2 | 1.12 | 1 | 1 | 1 | 1 | 1 | 1 | 1 | 1 | 0 | 1 | 1 | 1 | 1 | 1 | 1 | 1 |
|  | 4 | 1.12 | 1 | 1 | 1 | 1 | 1 | 1 | 1 | 1 | 1 | 2 | 1 | 1 | 1 | 1 | 1 | 2 |
|  | 2 | 0.28 | 1 | 1 | 0 | 0 | 1 | 1 | 0 | 1 | 0 | 1 | 1 | 0 | 0 | 1 | 0 | 1 |
| 4 | 2 | 5.6 | 2 | 4 | 2 | 3 | 3 | 3 | 4 | 2 | 1 | 4 | 4 | 1 | 2 | 4 | 2 | 3 |
|  | 4 | 5.6 | 2 | 4 | 2 | 4 | 4 | 3 | 4 | 2 | 1 | 4 | 4 | 3 | 4 | 4 | 2 | 4 |
|  | 2 | 1.12 | 1 | 1 | 0 | 0 | 2 | 2 | 0 | 1 | 0 | 2 | 4 | 0 | 1 | 1 | 0 | 1 |
|  | 4 | 1.12 | 1 | 1 | 0 | 1 | 3 | 2 | 0 | 2 | 1 | 3 | 4 | 0 | 1 | 1 | 1 | 2 |
|  | 2 | 0.28 | 0 | 0 | 0 | 0 | 1 | 1 | 0 | 0 | 0 | 1 | 1 | 0 | 0 | 1 | 0 | 0 |
| 3 | 2 | 5.6 | 2 | 1 | 2 | 2 | 3 | 3 | 1 | 2 | 1 | 4 | 3 | 2 | 1 | 2 | 2 | 4 |
|  | 4 | 5.6 | 2 | 1 | 2 | 2 | 4 | 3 | 1 | 2 | 2 | 4 | 4 | 3 | 2 | 3 | 3 | 4 |
|  | 2 | 1.12 | 1 | 0 | 1 | 1 | 1 | 1 | 1 | 1 | 1 | 2 | 2 | 1 | 0 | 1 | 1 | 1 |
|  | 4 | 1.12 | 1 | 0 | 1 | 0 | 2 | 1 | 0 | 1 | 1 | 3 | 2 | 1 | 1 | 2 | 2 | 2 |
|  | 2 | 0.28 | 1 | 0 | 0 | 0 | 1 | 1 | 0 | 1 | 0 | 1 | 0 | 0 | 0 | 0 | 1 | 1 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one active ingredient and from 5 to 95 parts by weight of an adjuvant in liquid of solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters petroleum sulfonates, sulfonated vegetable oils, polyoxyethylene derivatives of phenols and alkylphenols (particularly isoctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powders of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform and usually contains from 5 to about 95 parts by weight active ingredient, from about 0.25 to 25 parts by weight dispersant, and from about 4.5 to 94.5 parts by weight of water.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example, fertilizers, phytotoxicants and plant growth regulators, pesticides and the like used as adjuvants or in combination with any of the above-described adjuvants, it is preferred to employ the composition of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g., fertilizers, other phytotoxicants, etc., and applied in a single application. Chemicals useful in combination with the active ingredients of this invention either simultaneously or sequentially include, for example, triazines, ureas, carbamates, acetamides, acetanilides, uracils, acetic acids, phenols, thiolcarbamates, triazoles, benzoic acids, nitriles and the like.

Fertilizers useful in combination with the active ingredients include, for example, ammonium nitrate, urea, potash, and superphosphate.

When operating in accordance with the present invention, effective amounts of the glycinonitriles are applied to the plants, or to the parts thereof, in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific compound employed. In foliar treatment for the control of vegetative growth, the active ingredients are applied in amounts from about 0.25 to about 25.0 or more kilograms per hectare. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound of the formula

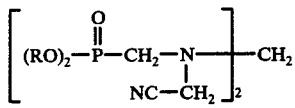

wherein R represents phenyl, naphthyl, substituted phenyl or substituted naphthyl, there being up to two substituents selected from halogen or alkyl, alkoxy and alkylthio of up to four carbon atoms.

2. A compound as defined in claim 1 wherein R is phenyl.

3. A compound as defined in claim 1 wherein R is tolyl.

4. A compound as defined in claim 1 wherein R is methoxyphenyl.

5. A compound as defined in claim 1 wherein R is xylyl.

6. A compound as defined in claim 1 wherein R is chlorophenyl.

7. A compound as defined in claim 1 wherein R is methylthiophenyl.

8. A compound as defined in claim 1 wherein R is chlorotolyl.

9. A herbicidal composition comprising a herbicidally effective amount of a compound of claim 1 and an inert diluent.

10. A herbicidal composition comprising a herbicidally effective amount of a compound of claim 2 and an inert diluent.

11. A herbicidal composition comprising a herbicidally effective amount of a compound of claim 3 and an inert diluent.

12. A herbicidal composition comprising a herbicidally effective amount of a compound of claim 4 and an inert diluent.

13. A herbicidal composition comprising a herbicidally effective amount of a compound of claim 5 and an inert diluent.

14. A herbicidal composition comprising a herbicidally effective amount of a compound of claim 6 and an inert diluent.

15. A herbicidal composition comprising a herbicidally effective amount of a compound of claim 7 and an inert diluent.

16. A herbicidal composition comprising a herbicidally effective amount of the compound of claim 8 and an inert diluent.

17. A herbicidal method which comprises contacting a plant with a herbicidally effective amount of a compound of claim 1.

18. A herbicidal method which comprises contacting a plant with a herbicidally effective amount of a compound of claim 2.

19. A herbicidal method which comprises contacting a plant with a herbicidally effective amount of a compound of claim 3.

20. A herbicidal method which comprises contacting a plant with a herbicidally effective amount of a compound of claim 4.

21. A herbicidal method which comprises contacting a plant with a herbicidally effective amount of a compound of claim 5.

22. A herbicidal method which comprises contacting a plant with a herbicidally effective amount of a compound of claim 6.

23. A herbicidal method which comprises contacting a plant with a herbicidally effective amount of a compound of claim 7.

24. A herbicidal method which comprises contacting a plant with a herbicidally effective amount of a compound of claim 8.

25. A process for preparing a compound of the formula

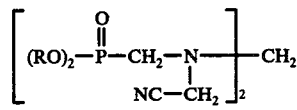

wherein R represents phenyl, naphthyl, substituted phenyl or substituted naphthyl, there being up to two substituents selected from halogen or alkyl, alkoxy and alkylthio of up to four carbon atoms, which comprises forming a mixture of a hindered phenylazomethine of the formula

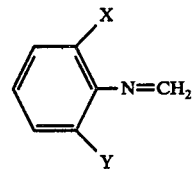

wherein X is lower alkyl and Y is lower alkyl, halogen or lower alkoxy, provided that X and Y cannot both be t-butyl, and a compound of the formula

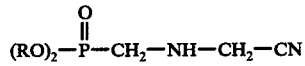

wherein R has the same meaning as above, and heating under vacuum until evolution of hindered aniline ceases.

26. A process as defined in claim 25 wherein a catalytic amount of a base is added to the mixture.

27. A process as defined in claim 25 wherein X and Y are ethyl.

28. A process as defined in claim 25 wherein the molar ratio of glycinonitrile to azomethine is about 2:1.

* * * * *